United States Patent [19]

Yang et al.

[11] Patent Number: 4,569,925
[45] Date of Patent: * Feb. 11, 1986

[54] PROCESS FOR PREPARING A VANADIUM PHOSPHORUS OXYGEN CATALYST COMPOSITION BY AN ORGANIC SOLUTION METHOD

[75] Inventors: Tai-Cheng Yang, Mahwah; Krishna K. Rao, Paterson; I-Der Huang, Upper Saddle River, all of N.J.

[73] Assignee: Exxon Research & Engineering Co., Florham Park, N.J.

[*] Notice: The portion of the term of this patent subsequent to Mar. 6, 2001 has been disclaimed.

[21] Appl. No.: 394,415

[22] Filed: Jul. 1, 1982

[51] Int. Cl.$^4$ .................. B01J 27/198; C07D 307/34
[52] U.S. Cl. ..................................... 502/209; 549/259
[58] Field of Search ................. 252/435, 437; 502/209

[56] References Cited

U.S. PATENT DOCUMENTS

| | | | |
|---|---|---|---|
| 3,288,721 | 11/1966 | Kerr | 252/435 |
| 3,864,280 | 2/1975 | Schneider | 252/435 |
| 3,907,707 | 9/1975 | Raffelson et al. | 252/437 |
| 3,915,892 | 10/1975 | Harrison | 252/435 |
| 3,975,300 | 8/1976 | Burress | 252/435 |
| 3,977,998 | 8/1976 | Freerks et al. | 252/435 |
| 3,985,775 | 10/1976 | Harrison | 260/346.75 |
| 4,016,105 | 4/1977 | Ken | 549/259 |
| 4,017,521 | 4/1977 | Schneider | 549/259 |
| 4,043,943 | 8/1977 | Schneider | 252/437 |
| 4,062,802 | 12/1977 | Bertolacini et al. | 252/435 |
| 4,111,963 | 9/1978 | Mount et al. | 260/346.75 |
| 4,122,096 | 10/1978 | Bertolacini et al. | 260/346.75 |
| 4,132,670 | 1/1979 | Katsumoto et al. | 549/259 X |
| 4,178,298 | 12/1979 | Stefani et al. | 252/435 X |
| 4,179,404 | 12/1979 | Barone | 252/435 |
| 4,181,628 | 1/1980 | Stefani et al. | 252/437 X |
| 4,187,235 | 2/1980 | Katsumoto et al. | 260/346.75 |
| 4,209,423 | 6/1980 | Hutchings et al. | 252/435 |
| 4,317,778 | 3/1982 | Blum et al. | 260/346.75 |
| 4,333,853 | 6/1982 | Milberger et al. | 252/435 |
| 4,416,803 | 11/1983 | Udovich et al. | 502/209 |
| 4,435,521 | 3/1984 | Yang et al. | 502/209 |

Primary Examiner—John Doll
Assistant Examiner—William C. Wright
Attorney, Agent, or Firm—Robert A. Maggio; Jack B. Murray, Jr.

[57] ABSTRACT

A process for preparing a vanadium, phosphorus oxygen containing catalyst composition capable of partially oxidizing hydrocarbons (e.g., n-butane) to form a carboxylic anhydride (e.g., maleic anhydride), and a process for using this catalyst to form such anhydrides is disclosed. The catalyst composition is prepared by an organic solution technique followed by activation in an air-hydrocarbon atmosphere.

13 Claims, No Drawings

PROCESS FOR PREPARING A VANADIUM PHOSPHORUS OXYGEN CATALYST COMPOSITION BY AN ORGANIC SOLUTION METHOD

BACKGROUND OF THE INVENTION

This invention relates to an improved process for preparing oxidation catalysts, and their use in a process for the preparation of carboxylic acid anhydrides from hydrocarbons. More particularly, it relates to a novel and simpler method for the production of vanadium-phosphorus-oxygen catalyst composites by an organic solution reducing method providing increased yields. Still more particularly, it relates to the production of maleic anhydride from n-butane, or n-butene, in a vapor phase process employing catalyst prepared by the process of the present invention.

Methods for the preparation of catalyst compositions of vanadium, phosphorus, and oxygen, and the use of these compositions as catalysts in hydrocarbon oxidations are known in the art.

Such preparative methods can be generally categorized as being aqueous-based or organic-based and employ either homogeneous solutions and/or heterogeneous mixtures (e.g., suspensions) of at least one of the components (e.g., a vanadium containing compound) which eventually forms the catalyst composition. V—P—O containing catalysts prepared by organic-based methods appear to be characterized at least by higher surface areas than those prepared by aqueous-based methods.

The particular method of preparation selected will depend on the various combination of properties sought to be imparted to the catalyst and the commercial attractiveness of the process. Particularly significant properties sought to be influenced by the catalyst preparative methods of the prior art include the vanadium valence, the P:V atomic ratio, the crystal phases of the catalyst, and the surface area of the catalyst.

While at least one patent seeks to impart a vanadium valence of less than +3.9, namely, U.S. Pat. No. 4,178,298, a majority of patents seek to obtain a vanadium valence between +4 and +5.

One preferred way of achieving this is to begin with vanadium in the +5 valence state and reduce the valency to less than +5 or alternatively to start with a vanadium compound having a valency of less than +5. A wide variety of reducing agents can be employed for the former reducing method approach. Representative of such reducing agents include acids such as hydrochloric, hydroiodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed are organic aldehydes such as formaldehyde and acetaldehyde; alcohols such as pentaerythritol, diacetone alcohol and diethanol amine. Additional reducing agents include hydroxyl amines, hydrazine, or nitric acid and the like.

Reducing methods also can be classified according to whether the vanadium compound is dissolved, e.g., solution reducing methods, or not, e.g., heterogeneous reducing methods.

In accordance with solution reducing methods, a vanadium compound having a valence of +5 such as $V_2O_5$ is dissolved in a solution containing the reducing agent. Because many strong acid reducing agents, such as HCl, also function to dissolve the vanadium compound, and, therefore, act as a solvent, the solvent and reducing agent can be the same (see for example Kerr, U.S. Pat. No. 3,288,721). Thus, a strong acid reducing agent (e.g., HCl) can be employed in an aqueous or non-aqueous (e.g., organic) medium to achieve dissolution and reduction therein. The phosphorus compound can be added to the vanadium compound for reaction therewith before or after vanadium reduction takes place.

After the aforedescribed reducing methods are employed, it is conventional to subject the resulting compositions to some type of activation procedure. The particular set of activation conditions which are employed depends on the initial treatment procedures employed in the preparation of the composition to be activated.

Thus, it is conventional to activate vanadiumphosphorus-oxygen containing compositions prepared by the aqueous-based solution reduction method by contacting the same with a reducing atmosphere such as CO, $H_2$, $H_2S$ and in the essential absence of added gaseous oxygen at temperatures of about 300° to 600° C. (see for example U.S. Pat. Nos. 4,062,802 and 4,122,096). Other activation methods applied to compositions prepared by aqueous-based solution reduction methods include: calcining in an inert atmosphere such as $CO_2$, $N_2$, a noble gas, or butane free oxygen (U.S. Pat. Nos. 3,907,707, and/or 4,178,298, and/or 4,111,963); calcining in oxygen (e.g., air) and then an inert atmosphere, e.g., $N_2$ or noble gas, (U.S. Pat. No. 3,977,998); calcining in air or an oxidizing gas alone (U.S. Pat. Nos. 3,907,707 and 4,111,963 where P:V atomic ratio is greater than 1:1; 3,915,892; and 4,179,404); and heating in a gaseous mixture containing air and a reducing component, e.g., butane (U.S. Pat. No. 3,915,892).

Organic-based heterogeneous reduction methods can be classified into those which reduce the vanadium compound in an organic slurry prior to or after contact with the phosphorus compound. For example, U.S. Pat. Nos. 4,132,670 and 4,187,235, which both contain essentially the same disclosure, are directed to an organic-based heterogeneous suspension type reduction method wherein $V_2O_5$ is first reduced with a suitable liquid organic medium, e.g., isobutanol, to impart a vanadium valence of between 4.0 and 4.6, and subsequently contacting the reduced vanadium compound with, for example, orthophosphoric acid to form a heterogeneous slurried reaction mixture of a suspended vanadium (IV) phosphate composition. This composition is recovered and calcined, i.e., activated, at about 380° C. by contact with a stream of air alone, and then a gaseous mixture of air and butane. The performance of the catalyst is disclosed as being severely dependent on this activation procedure (col. 7, lines 55–61 of U.S. Pat. No. 4,132,670).

European Patent Application Publication No. 0039 537, published Nov. 11, 1981 and based on U.S. patent application Ser. No. 146,971 filed May 5, 1980, now U.S. Pat. No. 4,333,853 discloses an organic heterogeneous slurry reducing method wherein a pentavalent vanadium compound and phosphorus compound are admixed prior to or subsequent to reducing the vanadium valence with, for example, isobutanol. The resulting catalyst precursor is calcined in air or an oxygen containing gas at a temperature of 250° to 600° C. Not only does this application fail to disclose the advantage of excluding air alone as an activation or calcination atmosphere, but as described in commonly assigned U.S. patent application Ser. No. 381,206 filed May 24, 1982 now U.S. Pat. No. 4,435,521 the catalyst of this EPA application performs better when activated in air alone relative to the exclusion of air alone in favor of an air and butane mixture.

U.S. Pat. No. 4,317,778 discloses a variety of V—P—O catalyst preparative methods, including aqueous and organic, solution and heterogeneous, reduction methods, all of which require the use of specific ratios of orthophosphoric and pyrophosphoric acids as the source of the phosphorus compound to minimize the solubility of the catalyst in water and thereby to enable the catalyst to be spray dried. The catalyst precursor is calcined in air or an oxygen containing gas at temperatures of 250° to 600° C. The catalyst precursor may also be calcined "either in the presence of hydrocarbon, in an inert gas, or both," (col. 6, lines 50 et seq.). This patent, however, does not disclose the particular combination of catalyst precursor preparative method and activation procedure of the present invention.

U.S. Pat. No. 3,985,775 discloses organic and aqueous solution reduction methods using HCl, as well as an organic heterogeneous method wherein vanadium is reduced and reacted with a phosphorus containing compound while the vanadium compound is suspended in an organic solvent (e.g., THF, example 14) to form a dihydrate precursor. However, it is suggested therein that even when employing an organic-based method, as much as 20 to 40% by weight of the liquid medium can be water (col. 6, lines 21-23). Furthermore, while several general classes of liquid organic media are disclosed, i.e., alcohols, ethers, and carboxylic acids, no Preference for alcohols is expressed nor is there any exemplification of the use of any alcohol in any organic based procedure. Numerous, i.e., eight, different complicated activation, i.e., pretreatment, procedures are also disclosed, only one of which avoids contact of the dihydrate with air alone, namely, pretreatment method H. However, pretreatment method H is only applied to an aqueous-based solution reduced dihydrate composition. The pretreatment procedure applied by exemplification to an organic-based heterogeneously reduced dihydrate, employs contact with air alone and then air and butane (example 14). Moreover, the results obtained using pretreatment H are inferior to a majority of the other pretreatment methods, and these results are reported after 530 hours run time, more than twice the run time of any other catalyst prepared by other pretreatment methods. Thus, this reference provides no suggestion of selecting the operative preparative variables to include an organic solution reduction method to form a catalyst precursor, and activation of the resulting precursor in a hydrocarbon-air atmosphere.

U.S. Pat. No. 3,975,300 is directed to a onestep method for preparing vanadium-phosphorus composites wherein a paste comprising an organic reducing agent, e.g., ethylene glycol, phosphoric acid, and a vanadium compound is formed and then evaporated to dryness. The dried composition is then optionally conditioned in a hydrocarbon-air mixture at about 450° C. This process differs from the process of U.S. Pat. No. 4,132,670 in that reduction of vanadium takes place in the presence of phosphoric acid and a slurry or suspension of the components of the paste is never prepared.

Activation methods for vanadium-phosphorus-oxygen containing compositions prepared by organic-based solution reduction methods can be conducted by heating in air alone and then a gaseous mixture of air and butane. An illustration of this type of activation procedure is found in U.S. Pat. Nos. 3,864,280 and 4,017,521. Activation in air alone is disclosed in U.S. Pat. No. 4,179,404. U.S. Pat. No. 4,043,943 discloses an organic-based solution reduction method wherein a vanadium phosphate compound is precipitated from a liquid organic medium and activated. While it is broadly disclosed (col. 10, lines 16 to 23) that the average vanadium valence can be varied somewhat by oxidative or reductive treatment after precipitation as by subjecting the precipitated solid to an oxidizing or reducing atmosphere, these treatments are a less preferred substitution for the use of a suitable oxidizing or reducing reagent to impart a vanadium valence of 3.8 to 4.6, and do not constitute or perform the function of activation. The activation procedure is described at col. 2, lines 59–62, i.e., calcination at a temperature of 100° to 500° C., and at col. 12, lines 29 to 32, i.e., in an atmosphere of air alone and then a mixture of air and butane.

Thus, none of the prior art appears to be directed to preparing a V—P—O containing composition by an organic-based solution reduction method followed by activation in an atmosphere which excludes air alone at any time during the activation procedure.

In view of the above, there has been a continuing search for ways to improve the yield of V—P—O containing catalysts prepared by organic solution reduction methods. The present invention is a result of this search.

SUMMARY OF THE INVENTION

In one aspect of the present invention there is provided a process for preparing a vanadium phosphorus oxygen containing composition capable of catalyzing the oxidation of hydrocarbons which comprises:

(a) reacting at least one vanadium containing compound with at least one phosphorus containing compound in a liquid organic media in a manner and under conditions sufficient to form a vanadium phosphorus oxygen containing catalyst precursor composition having a phosphorus to vanadium atomic ratio of from about 0.5:1 to about 2:1 and an average vanadium valence of from about 3.9 to about 4.7, said vanadium and phosphorus containing compounds being dissolved in said liquid organic media during said reaction;

(b) separating the catalyst precursor composition from the organic media; and (c) activating the catalyst precursor composition by contact with an atmosphere comprising air and at least one hydrocarbon.

In another aspect of the present invention there is disclosed a process for using the catalyst prepared by the aforementioned process to oxidize hydrocarbons.

DESCRIPTION OF THE PREFERRED EMBODIMENTS

I. Preparation of Catalyst Precursor

In accordance with the process of the present invention, a vanadium containing compound and a phosphorus containing compound are dissolved and reacted in a liquid organic media to form a catalyst precursor which is then isolated and activated. The term "media" is used herein in a collective sense to signify singular and/or plural.

The vanadium compound functions as a source of vanadium and its identity is not critical subject to the considerations described hereinafter. Accordingly, any vanadium containing compound which additionally can comprise halogen; preferably oxygen, oxygen and hydrogen, or oxygen, hydrogen and carbon, may be employed. The particular vanadium containing compound selected must be capable of producing an average vanadium valence in the catalyst precursor of between about 3.9 and about 4.7.

The initial average vanadium valence of the vanadium containing compound is preferably at least +5 although lower initial average vanadium valences of between +4 and +5, and even lower, are acceptable provided reaction conditions are controlled to impart the required average vanadium valence to the catalyst precursor. For example, if over-reduction of the vanadium occurs, or if the average vanadium valence of the initial starting compound is below about 3.9, a suitable oxidizing agent can be employed to achieve the proper valence.

The vanadium containing compound is also selected in conjunction with the organic liquid media so that it is capable of being dissolved therein and of achieving the appropriate valence as described herein. Thus, solubilization and reduction of the vanadium compound can be achieved by the appropriate selection of organic media and vanadium compound such that the vanadium compound is naturally soluble in the latter at reaction temperatures, e.g. vanadium (IV) and (V) oxychloride and bromide salts are soluble in the oxygenated organic media described herein. Alternatively, vanadium compounds which are insoluble in the organic media, such as $V_2O_5$, can be solubilized by interaction of the vanadium compound as a dispersed solid in the organic media with a suitable solubilizing agent. Such solubilizing agents include well known reducing agents as described above, particularly hydrogen chloride or hydrogen bromide. In cases where dissolution of the vanadium compound is slow, the application of a hydrogen halide acid, is a useful, conventional, and preferred means of achieving solubilization as well as aiding in the reduction of the vanadium compound to the appropriate valence state. Solubilization techniques are conventional in the art and include introducing a stream of anhydrous hydrogen chloride gas through a suspension of the vanadium containing compound. See for example U.S. Pat. No. 4,043,943 the disclosure of which is herein incorporated by reference.

Representative of vanadium compounds which can be employed in the preparation of the catalyst precursor include vanadium oxides, such as vanadium tetroxide, vanadium pentoxide and vanadium trioxide; vanadium halides and oxyhalides, such as vanadium trichloride, vanadium tribromide, vanadyl chloride, vanadyl trichloride, vanadyl dichloride, vanadyl bromide, vanadyl dibromide and vanadyl tribromide; vanadium-containing acids, such as metavanadic acid and pyrovanadic acid; and vanadium salts, both organic and inorganic, such as ammonium metavanadate, vanadium sulfate, vanadium oxysulfate, vanadium phosphate; vanadyl formate, oxy vanadium (IV) carboxylate, vanadyl acetocetonate, vanadyl oxalate, vanadyl alkoxides, and mixtures thereof. Vanadium pentoxide is, however, preferred.

The phosphorus containing compound useful as a source of phosphorus in the catalyst precursor is well known in the art. Suitable phosphorus containing compounds include phosphoric acid, such as metaphosphoric acid, orthophosphoric acid, triphosphoric acid and pyrophosphoric acid; phosphorus oxides, such as phosphorus pentoxide; phosphorus halides and oxyhalides, such as phosphorus oxyiodide, phosphorus pentachloride and phosphorus oxybromide; phosphorus salts such as mono-, di-, and tri-ammonium phosphates; and organophosphorus compounds, such as ethyl phosphate and methyl phosphate as well as mixtures thereof.

However, the phosphoric acids, such as orthophosphoric acid and pyrophosphoric acid and mixtures thereof are preferred. More specifically, phosphoric acid generally will be employed as an aqueous solution or mixture having a concentration of typically at least 85%, preferably at least 90%, and most preferably at least 95%, by weight, based on the weight of the solution or mixture. Substantially anhydrous phosphoric acid, e.g., orthophosphoric acid is also preferred. Polyphosphoric acid is another type of anhydrous phosphoric acid. This acid is commercially available as a mixture of orthophosphoric acid with pyrophosphoric, triphosphoric and higher acids, and is sold on the basis of its calculated content of $H_3PO_4$, as for example 115%. Superphosphoric acid is a similar mixture sold at 105% $H_3PO_4$. These acids revert primarily to orthophosphoric acid upon dilution with water.

The liquid organic media functions as a solvent at reaction temperature for the vanadium containing compound, as a solvent for the phosphorus containing compound, where needed a mild reducing agent for the vanadium containing compound, and as a solvent for the catalyst precursor at reaction temperature but as a suspending media at some temperature below reaction temperature to permit separation of the catalyst precursor from the solution. Thus, while any liquid organic media which is capable of performing preferably all, of the aforenoted functions can be employed, such media is preferably comprised of carbon, hydrogen, and optionally but most preferably a hetero-atom such as oxygen, or a functional equivalent of oxygen, i.e. nitrogen, or sulfur. Included within the scope of liquid organic media are alcohols, aldehydes, ketones, esters, ethers, acids, amines, amides, and thiols, and mixtures thereof as well as compounds of mixed functionality such as ether acids, and ether alcohols. The compounds constituting such organic media contain typically from about 1 to about 20, preferably from about 1 to about 10, and most preferably from about 1 to about 5 carbon atoms.

More specifically, the organic moiety to which the alcohol, aldehyde, carboxyl, ketone, amide, ether, ester, amine, and thiol functional groups can be attached includes alkyl, typically about $C_1$ to about $C_{20}$, preferably $C_1$ to $C_{10}$, most preferably $C_1$ to $C_5$ alkyl; aryl, typically about $C_6$ to about $C_{14}$, preferably about $C_6$ to about $C_{10}$, most preferably $C_6$ aryl, cycloalkyl, typically about $C_4$ to about $C_{20}$, preferably about $C_6$ to about $C_{12}$, most preferably about $C_6$ to $C_{10}$ cycloalkyl, aralkyl and alkaryl wherein the alkyl and aryl groups thereof are described above.

Each class of liquid organic media can contain one or more, typically 1 to 3, functional groups and mixtures of functional groups. The organic media may also include non-oxygenated unreactive diluents which are in the liquid phase at reaction temperature. These include hydrocarbons, mono- and polychlorinated hydrocarbons, and the like diluents.

For the useful effect in the increasing of the surface area of the final neat catalyst composition, the organic liquid media preferably will contain an appreciable amount of an oxygen-containing organic compound. The effective amount varies depending upon the particular compound(s) employed. In general, a volume percent of at least 15 percent will be satisfactory. Preferably, the entire liquid media is an oxygen-containing compound or a mixture of oxygen-containing compounds.

Representative organic compounds useful as the liquid organic media and as components of a suitable liquid media herein include methanol, ethanol, 1-propanol, 2-propanol, isobutanol, 1-butanol, 2-butanol, t-butylalcohol, 3-methyl-2-butanol, 1-pentanol, 2-pentanol, 3-pentanol, 2-methyl-1-butanol, 3-methyl-1-butanol, 2,2-dimethyl-1-propanol, 1-hexanol, 4-methyl-1-pentanol, 1-heptanol, 4-methyl-1-hexanol, 3-ethyl-1-pentanol, 1-octanol, 2-ethyl-1-hexanol, 4-methyl-1-heptanol, 2-propyl-1-pentanol, 1-dodecanol, 4-propyl-1-nonanol, 1-tetradecanol, 4,5-dimethyl-1-decanol, 2,4-trimethyl-1-pentanol, 2,4,6,8-tetramethyl-1-decanol, cyclopentanol, xylenol, benzyl alcohol, 1,2-ethanediol, 1,2-propanediol, 1,4-butanediol, 1,8-octanediol, 1,2-tetradecanediol, glycerol, trimethylol propane, diethylene glycol, triethylene glycol; cyclohexanol, 2-methoxy-1-ethanol, 2-ethoxy-1-ethanol, 4-methoxy-1-butanol, 3-phenyl-1-propanol, 2-cyclohexyl-1-ethanol, tetrahydrofurfuryl alcohol, acetic, propionic, butyric, glycollic, pentanoic, hexanoic, methoxyacetic, ethoxyacetic, butoxyacetic acids; diethyl ether, dipropyl ether, dibutyl ether, tetrahydrofuran, 1,4-dioxane, tetrahydropyran, 1,4-dimethoxy butane, 1,4-diethoxy butane, dimethoxy ethane; methyl acetate, ethyl acetate, propyl acetate, butyl acetate, pentyl acetate, hexyl propionate, methyl propionate, ethyl propionate, n-butyl propionate, 2-ethyl-1-hexyl acetate, dimethyl succinate, diethyl succinate, diethyl adipate, 2-methoxy-1-ethyl acetate, ethyl methoxy acetate, methyl tetrahydrofuroate, methyl benzoate; formaldehyde, acetaldehyde, propionaldehyde, m-tolualdehyde, trioxane; acetone, methyl ethyl ketone, methyl isobutyl ketone, cyclohexanone, dimethyl ketone, diethyl ketone, dibutyl ketone, benzophenone; ethylene diamine, hexylamine, cyclohexyl amine, diethylamine, 1,3-butadiamine, ethylene triamine, n-phenylbenzamine; formamide, dimethyl formamide, acetamide, 3-butaneamide, n-phenyl acetamide, azacyclohexan-2-one, hexane diamide; phenylmethane thiol, ethane thiol, pentane thiol, 1,4-butanedithiol, cyclohexane thiol, benzylthiol, 1,5-pentanedithiol, 2-acetoxy-1-ethanol, methyl lactate, 4-methyl-3-penten-1-ol, phenol, p-cresol, thylmol, phenylacetic acid, 4-methyl-3-pentenoic acid, hexahydrobenzoic acid, anisol; inertly substituted oxygen-containing compounds such as 2-chloro-1-ethanol, 3-bromo-1-propanol, 2,2-di(-chloromethyl)-1-ethanol, 3,4-dibromo-1-hexanol, 2,2,2-trichloroethanol, 2-chloro-3-bromo-1-heptanol, 4-chloro-2-ethyl-1-hexanol, 2,4,6-trichloro-1-decanol; chloroacetic, dichloroacetic and trichloroacetic acids, 2-chloropropionic, 2,2-dichloropropionic, 2,2,3-trichloropropionic acids; bromoacetic, 4-bromohexanoic, 4,6-dibromooctanoic, 3,chloro-4-bromopentanoic acids; 3-chlorotetrahydrofuran, 3-bromotetrahydrofuran, 2,2-dibromoethyl ether, 3,3-dichlorodipropyl ether, 3,4-dichlorotetrahydrofuran, 3-bromotetrahydropyran; methyl chloroacetate, ethyl chloroacetate, propyl chloroacetate, 2-chloroethyl chloroacetate, 2-bromopropyl dichloroacetate, pentyl trichloroacetate, butyl bromoacetate, and the like oxygen-containing and inertly substituted oxygen-containing compounds.

Representative compounds which can function as a diluent in the organic media include hexane, heptane, octane, cyclohexane, methylcyclopentane, 2,2,4-trimethylpentane, dodecane, 2-ethylhexane, 3-octene, cyclohexene; benzene, toluene, o-xylene, m-xylene, p-xylene, ethylbenzene, trimethylbenzene, 2-propylbenzene; methylene chloride, chloroform, carbon tetrabromide, carbon tetrachloride 3-chlorohexane, 2,3-dichlorooctane, chlorocyclohexane, 1,2-dichloropentane, 1,2-dichloroheptane, 1,1,2-trichloroethane; chlorobenzene, bromobenzene, o-dichlorobenzene, p-dichlorobenzene, 2-chlorotoluene, 4-chlorotoluene, 2,4-dichlorotoluene, 1,3-dimethyl-4-chlorobenzene, butyl bromide, and the like hydrocarbons and halogenated hydrocarbons.

Preferred organic liquid media include alcohols, aldehydes, ethers, and ketones.

The most preferred compounds for use as the organic media are the primary and secondary alcohols. Alcohols which contain 1, 2 or 3 hydroxyl substituted groups are especially preferred because these, in general, are readily liquified at useful temperatures in the process range.

The most preferred organic alcohol is isobutanol.

The precursor forming reaction is conducted by providing a reaction solution comprising the liquid organic media having the vanadium compound and phosphorus compound dissolved therein. Where the vanadium compound must be solubilized in the organic media, with for example HCl, this is preferably done prior to addition of the phosphorus compound.

The molar ratio of vanadium compound to phosphorus compound in the reaction solution is controlled in a manner sufficient to achieve a P:V atomic ratio in the catalyst precursor of from about 0.5:1 to about 2:1, preferably from about 0.9:1 to about 1.5:1, and most preferably from about 1:1 to about 1.3:1 (e.g., 1.2:1).

The liquid organic media is present in the reaction solution in the amount effective to reduce and/or assist in reducing where needed, the vanadium compound to achieve the described valence, to dissolve it and the resulting catalyst precursor, and to dilute the phosphorus compound as well as the other components of the reaction mixture to the extent that uniform heating and mixing of the reactants is possible.

Thus, while any effective amount of organic media can be employed in the reaction solution, such effective amounts typically will constitute from about 15 to about 98%, preferably from about 20 to about 95%, and most preferably from about 30 to about 85%, by weight of the solution, based on the combined weight of vanadium and phosphorus compounds and organic media.

The reaction solution is heated to temperatures and for periods effective to cause the vanadium and phosphorus compounds to react and preferably to achieve an average vanadium valence in the precursor of between 3.9 and 4.7, (e.g., 4.0 and 4.3). The identity of the liquid organic media is preferably selected so that it will reflux at the selected reaction temperature. Thus, while the reaction mixture can be heated to any effective reaction temperature, such effective temperatures will typically vary from about 25° to about 300° C. (e.g., 30° to 110° C.), preferably from about 60° to about 200° C., (e.g. 60° to 110° C.) and most preferably from about 80° to about 150° C., for periods which typically will vary from about 1 to about 50 hours, preferably from about 10 to about 35 hours, and most preferably from about 15 to about 25 hours. When isobutanol is used as the organic media, simple refluxing at about 105°–110° C. (1 ATM) for a period of from about 1 to about 2 hours will suffice. The reaction solution is preferably maintained in the substantially anhydrous, most preferably anhydrous, state by removing water formed in-situ by azeotropic distillation or other suitable means. By "substantially anhydrous" as used herein is meant typically less than about 20%, preferably less than about 10%, and most preferably less than about 5% (e.g., less than 1%), by weight water, based on the weight of the organic media in the reaction mixture.

The reaction pressure is not critical and can be subatmospheric, atmospheric, or superatmospheric provided the reactants and liquid organic media do not volatilize to the extent that the composition of the reaction mixture is altered from the description provided herein. Atmospheric pressure is preferred.

It is also believed to be preferable to conduct the catalyst precursor forming reaction under sufficient agitation to assure uniform reacting, and interaction between the reactants, during reaction. This can be achieved by conventional high speed agitation equipment capable of achieving a high degree of mixing.

Upon completion of the reaction, the catalyst precursor is separated from the reaction solution by any means capable of achieving this goal. This separation can be accomplished in a variety of ways. Generally, it takes place in several stages, e.g., by precipitation of the catalyst precursor from solution, bulk separation, and final purification, e.g. by drying. Precipitation is conducted in accordance with conventional techniques including pH adjustment, removal of the solvent by evaporation, or distillation, cooling of the medium, selective removal by distillation of a good solvent component from a medium composed of a mixture of good and poor solvent components, addition of a poor solvent to the liquid medium, creating a super-saturated liquid medium by mixing two solutions each containing different reactants, a combination of these operations and the like.

Where the precipitation method employed produces a slurry of the catalyst precursor, bulk separation techniques such as, filtration, centrifugation, decantation, and evaporation can then be applied. To facilitate precipitation, the polarity of the reaction solution can be reduced in accordance with the procedures described in U.S. Pat. No. 4,043,943 which has already been incorporated herein by reference. If a hydrogen halide has been employed to dissolve the vanadium compound, it can be evolved and removed from the reaction solution during the precursor separation procedure, e.g. by distillation, or by washing and neutralization.

The precursor solids, after bulk separation, are then typically subjected to conditions sufficient to remove any residual liquid organic media. This can be achieved by drying, preferably continuous drying, to evaporate residual organic liquid media, by washing the precursor solids with water, or by employing both procedures. Before final purification is conducted, the separated catalyst precursor solids can be washed in the liquid organic media one or more times to remove any residual unreacted phosphorus compound and/or any other organic soluble species followed by a repetition of bulk separation procedures.

Drying can be achieved by exposing the precursor to air at room temperature for a period of from about 1 to about 100 hours or by placing it in a forced hot air oven maintained at a temperature of less than about 180° C. typically between about 60° and about 150° C. for about 1 to about 5 hours. Alternatively, the precursor can be air dried at room temperature for between about 1 and about 48 hours and then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

The resulting catalyst precursor has an average vanadium valence of typically between about 3.9 and about 4.7, preferably between about 3.9 and 4.4, most preferably between about 3.9 and about 4.1; a P:V atomic ratio of typically from about 0.5:1 to about 2:1, (e.g., about 0.6:1 to about 2:1) preferably from about 0.9:1 to about 1.5:1, most preferably from about 1:1 to about 1.3:1. Generally the P:V atomic ratio is at least 1:1 and not more than 1.4:1.

The average vanadium valence is defined herein as the sum of the products of the mole fraction of total vanadium in each valence state times said valence, said sum covering all the valences present.

II. Activation of the Catalyst Precursor

The catalyst precursor must be activated in order to produce a final catalyst capable of exhibiting the improved yields illustrated herein. Activation, i.e., heating of catalyst in a selected atmosphere at a selected elevated temperature, can be accomplished in a separate step or insitu in the reactor in which it will be used for the oxidation of hydrocarbons. Activation temperatures will vary slightly depending on whether the final catalyst will be employed for fixed bed or fluidized bed operations. Thus, for fixed or fluid bed operations, activation temperatures typically will vary from about 200 to about 450, preferably from about 250 to about 410, and most preferably from about 300° to about 410° C.

The atmosphere in contact with the fresh catalyst during activation will affect the performance of the catalyst. If activation is conducted in air alone and then in a mixture of air and a suitable hydrocarbon, the catalyst performance will suffer significant reductions in yield.

Thus, it is critical to the process of the present invention that activation be conducted in a gaseous atmosphere comprising air and a hydrocarbon and in the substantial absence of air alone.

More specifically, suitable activation atmospheres comprise and preferably consist essentially of a mixture, preferably a non-explosive mixture, of air and any hydrocarbon, preferably any hydrocarbon, described hereinafter which can be oxidized in accordance with the process of the present invention for using the catalyst.

Generally, in a fixed bed operation, the activation atmosphere will conveniently comprise a non-explosive mixture of air and the hydrocarbon to be oxidized by the catalyst.

Preferred hydrocarbons for use in activation include methane, ethane, propane, butane, butene, butadiene and pentane.

The mole fraction of gaseous components in the activation atmosphere typically will be outside the explosive limits of the mixture.

Thus, when the activation atmosphere comprises air and butane, such mixtures preferably will contain, for example, between about 0.1 to about 1.8 (e.g., 1.0 to 1.2) mole % butane or above about 24 mole % butane.

Although not essential, it is desirable to maintain a steady flow of the activation atmosphere over the catalyst precursor surface during activation. Flow rates typically will be sufficient to provide a contact time with the catalyst of about 1 to about 10, preferably from about 1 to about 5, and most preferably from about 1 to about 3 seconds. Thus, suitable flow rates or space velocities of the activating atmosphere may be manipulated by one skilled in the art to achieve the desired contact time.

The period of activation will depend on the particular activation temperature and atmosphere selected as well as the contact time. Generally, such activation periods at the aforedescribed activation temperatures and in the presence of a non-oxidizing atmosphere will typically vary from about 0.5 to about 72, preferably from about 1 to about 48, most preferably from about 1 to about 24 hours.

The preferred method of activation is to place the catalyst precursor in the reactor in which it will be employed and pass a gaseous mixture of air and butane in continuous flow over the catalyst precursor at temperatures of between about 300° and 410° C. until the conversion of the butane reaches about 90% on a molar basis. The temperature of the feed stream is then lowered to reaction temperature and product produced as desired. Thus, this activation procedure is simple and easy to achieve and actually produces collectable product during the course thereof.

III. Catalyst Shaping

At some point in their preparation, the catalysts described herein preferably are formed into structures suitable for use in a reactor, although unshaped, powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax ®, Methocel ®, Avicel ®, graphite, and the like. Extrusion of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titania-silica. Spray dried catalysts can also be employed for fluidized bed operations.

The preferred shape for fixed bed operations is a cylindrical pellet having a hollow core running through the center thereof or an extrudate.

A catalyst support, if used, provides not only the required surface for the catalyst, but gives physical strength and stability to the catalyst material. The carrier or support typically possesses a surface area of from about 0.1 to about 200, preferably from about 1 to about 50, and most preferably from about 5 to about 30 m$^2$/g. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90, preferably from about 5 to about 80%, by weight, based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. The supports may be of a variety of shapes, the preferred shape of the supports is in the shape of cylinders or spheres.

The particle size of a supported or unsupported catalyst used in fluidized beds is quite small, usually varying from about 10 to about 200 microns. Typically the attrition resistance of such catalysts is improved by the presence of zirconium or other modifier capable of hardening the catalyst. This can be achieved by the addition of oxides of the appropriate metal during preparation of the catalyst precursor.

Inert diluents such as silica or TiO$_2$ may be present in the catalyst, but the combIned weight of the essential active ingredients of vanadium, oxygen and phosphorus should preferably consist essentially of at least about 10, preferably at least about 30% by weight, based on the total weight of catalyst and support.

Shaping of unsupported catalyst can be conducted prior or subsequent to activation of the catalyst precursor. Preferably, shaping of the unsupported catalyst is conducted on the catalyst precursor prior to activation. The point during which shaping with supports or carriers is conducted will vary with the type of support. Solid supports, such as silica alumina, can be added to the reaction solution during the formation of the catalyst precursors.

IV. Stability Additives

In addition to vanadium, phosphorus, and oxygen, the catalyst of the present invention may also comprise effective amounts of stability additives which have been designated herein as promoters and/or activators. The typical additives which are used include magnesium, calcium, scandium, yttrium, lanthanum, uranium, cerium, chromium, manganese, iron, cobalt, nickel, copper, zinc aluminum, gallium, indium, silicon, germanium, tin, bismuth, antimony, tellurium, lead, titanium, hafnium, lithium, potassium, cesium, zirconium, and mixtures thereof.

The promoters and/or activators are readily introduced into the catalyst during formation of the catalyst precursor by admixture with the vanadium and phosphorus compounds during the heating in the organic liquid media. These promoter and activator compounds, however, should be at least partially soluble in the solvent medium used in the particular preparation in order to be best suited for combination with the phosphorus and vanadium components of the catalyst. Typical compounds of titanium, which is the preferred activator, include titanium oxides, such as titanium oxide, titanium dioxide, titanium trioxide, titanium sesquioxide, titanium pentoxide, titanium halides such as titanium dichloride, titanium trichloride, titanium tetrachloride, titanium dibromide, titanium tribromide, titanium diiodide, titanium triiodide, titanium tetraiodide, and titanium tetrafluoride; titanium salts such as titanium phosphates and titanium sulfates; and organic titanium compounds, e.g., alkyl titanates such as methyl titanate, ethyl titanate, isopropyl titanate and butyl titanate and aryl titanates such as phenoxy titanium trichloride and phenyl titanate. Typical compounds of zinc (illustrative of activators as a class) are metallic zinc, zinc oxide, zinc chloride, zinc bromide, zinc iodide, zinc formate, zinc nitrate or zinc acetate.

V. Catalyst Composition

The P:V atomic ratio of the activated catalyst typically can vary from about 0.9:1 to about 1.6:1, preferably from about 1:1 to about 1.4:1, and most preferably from about 1:1 to about 1.2:1 (e.g. 1:1 to 1.13:1).

The average vanadium valence of the activated catalyst can vary typically from about 3.9 to about 4.7, preferably from about 3.9 to about 4.4, and most preferably from about 3.9 to about 4.2 (e.g. 4.0).

The surface area of the activated unsupported catalyst is typically controlled to be greater than 5 m$^2$/g, preferably greater than 10 m$^2$/g, and can vary typically from about 10 to about 100, preferably from about 10 to about 50, and most preferably from about 10 to about 40 m$^2$/g (e.g. 10 to 25 m$^2$/g).

The above properties are determined by the following analytical methods.

The average vanadium valence is determined from magnetic susceptibility measurements performed from 77° to 300° K. using the Faraday technique. Contributions due to ferromagnetic impurities are removed prior to evaluation of the data. The measurements are carried out in an applied field of 6.35 kG. The average vanadium valence is determined from the Curie constant determined from plots of inverse susceptibility versus temperature, as are the Weiss temperatures, $\theta$.

Phosphorus to vanadium atomic ratio is determined by elemental analysis wherein vanadium is quantified by atomic absorption spectroscopy following acid digestion of the catalyst; quantification of phosphorus is conducted by gravimetric analysis using precipitation as the phosphomolybdate.

Surface area is determined by the BET method, the general procedures and theory for which are disclosed in H. Brunaur, P. Emmett, and E. Teller, J. of Am. Chem. Soc. Vol. 60, p. 309 (1938).

VI. Vapor Phase Oxidation of Hydrocarbons

The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g. 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methyldiene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes, which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffinic or naphthenic petroleum sources. Full boiling range naphthas (boiling within the range of about 35°–230° C. ) can be used but it is Preferred to use light naphtha cuts boiling within the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane pentane or isopentene to citraconic anhydride, maleic anhydride and α-carboxy maleic anhydride; pseudocumene to trimellitic anhydride; durene to pyromellitic anhydride; and o-xylene to phthalic anhydride.

A preferred hydrocarbon feed for the catalyst of the present invention for conversion to maleic anhydride is a n-C$_4$ hydrocarbon comprising a predominant amount of n-butane and more preferably at least 90 mol percent n-butane. In the following discussion and exemplification, therefore, butane is used in most examples to demonstrate (but not to limit) the use of the catalysts made by the process of this invention for producing maleic anhydride. It is contemplated that mixtures rich in butane can also be used, such as typical butane-butene refinery streams.

Preparation of Maleic Anhydride

The oxidation of n-butane to maleic anhydride may be accomplished by contacting n-butane, typically at low concentrations with oxygen in the presence of the described catalyst. Air is entirely satisfactory as a source of oxygen but synthetic mixtures of oxygen and diluent gases, such as nitrogen, carbon dioxide and the like also may be employed. Air enriched with oxygen may be employed.

The gaseous feed stream to the oxidation reactors normally will contain air and typically from about 0.5 to about 10, preferably from about 1 to about 8, and most preferably from about 1.2 to about 5 mole % butane. About 1.0 to about 1.9 mole % of the butane in air is satisfactory for optimum yield of product for the process of this invention using a fixed bed reactor, and from about 2.5 to 4.0 mole % butane using a fluidized bed. Although higher concentrations may be employed, explosive hazards may be encountered. Lower concentrations of butane less than about 1%, of course, will reduce the production rate obtain at equivalent flow rates and thus are not normally economically employed.

Flow rates of the gaseous feed stream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained A variety of reactors will be found to be useful and multiple tube heat exchanger type reactors are quite satisfactory. The tubes of such reactors may vary in diameter typically from about ¾ inch to about 2 inches, and the length may be varied from about 3 to about 15 feet.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon-steel, nickel, glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the butane concentration. Under usual operating conditions, in compliance with the preferred procedure of this invention, the average bed temperature referred to herein as the reaction temperature, measured by thermocouples disposed in the reactor, is typically from about 350 to about 450, preferably from about 360 to about 420, and most preferably from about 370° to about 410° C. Described another way, in terms of salt bath reactors with reactor tubes about 1.5 inches in diameter, the exit salt bath temperature will typically be controlled from about 330 to about 430, preferably from about 340 to about 400, and most preferably from about 350° to about 390° C. Under normal conditions, the temperature in the reactor ordinarily should not be allowed to go above about 450° C. for extended lengths of time because of decreased yields and possible deactivation of the novel catalyst of this invention.

The reaction may be conducted at atmospheric, superatmospheric or below atmospheric pressure.

The maleic anhydride may be recovered by a number of ways well known to those skilled in the art. For example, the recovery may be by direct condensation or by absorption in suitable media, with subsequent separation and purification of the maleic anhydride.

While the above discussion is directed primarily to the use of a butane containing feed gas, it is equally applicable to the use of other hydrocarbon feed gases described herein subject to any modifications which would be obvious to one skilled in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples the reactor used to test the catalyst is described as follows:

The reactor is U-shaped with one arm as the preheater (empty) and the other arm for packing catalyst. The reactor tube for the catalyst bed has a ⅜" O.D., 0.305" I.D., and 7 inches in length, and is made of a stainless steel tube. Five cc of catalyst is charged to the reactor for testing and a 1/16 inch outer diameter thermocouple is placed 1 inch from the inlet of the catalyst bed to measure the reaction temperature. The reactor tube is immersed in a HITEC ® salt bath. Reactor inlet pressure is about 1 psig. Once a catalyst evaluation is started, the reaction is continued without interruption until the end of a series of runs. Recoveries are made at convenient time intervals. During a recovery, a scrubber with deionized water is placed in an ice-water bath and is connected to the reactor effluent to trap maleic anhydride and other condensable products. The scrubber effluent is connected to an on-line gas chromatograph for tail gas analysis. Maleic anhydride is titrated as maleic acid along with other acids using a potentiometer. Carbon balance is calculated according to the number of g-atoms of carbon in the reactor effluent to the g-atoms of carbon fed to the system.

Conversion of butane is calculated according to the following equation:

$$\% \text{ butane conversion} = \frac{\text{g moles of reacted butane}}{\text{g moles of butane fed}} \times 100$$

Maleic anhydride yield is calculated according to the following equation:

$$\% \text{ MA yield} = \frac{\text{g moles of maleic anhydride produced}}{\text{g moles of butane fed}} \times 100$$

The selectivity of maleic anhydride is calculated according the the following equation:

$$\% \text{ selectivity of MA} = \frac{\text{g moles of maleic anhydride produced}}{\text{g moles of butane reacted}} \times 100$$

Unless otherwise specified, all of the catalysts prepared in accordance with the following examples of the present invention possess a P:V atomic ratio of between 1:1 and 1.2:1, an average vanadium valence of 3.9 to 4.1, and a surface area of 5 to 15 m²/g. Furthermore, all preparations of the first catalyst precursor are conducted using azeotropic distillation to remove water and other low boiling components formed in-situ.

EXAMPLE 1 replaced with a mixture of air-butane (1.2 mole % butane) (contact time 2 sec.) for the remainder of the experiment. Samples are analyzed after varying on-stream times as reported in Table 1 and the results summarized at Table 1, runs 6 to 9.

Comparing the results of Example 1 with Comparative Example 1, it can be seen that substantially superior results in both yield and selectivity at comparable on-stream times are obtained by the activation method of the present invention.

TABLE I

| | | Activation | | | Reaction Conditions | | | | | | |
|---|---|---|---|---|---|---|---|---|---|---|---|
| Example No. | Run No. | % Butane in air | Contact Time (Sec.) | Temp °C. | % Butane in air | Contact Time (Sec.) | Temp (°C.) | Hours on Stream | Maleic Anhydride (M.A.) Yield mole % | Butane Conversion % | Selectivity % |
| Example 1 | 1 | 1.2 | 2 | 400 | | | | 24 | 49.6 | 85.4 | 58.1 |
| | 2 | | | | 1.2 | 2 | 400 | 48 | 44.8 | 78.9 | 56.8 |
| | 3 | | | | 1.2 | 2 | 400 | 72 | 42.5 | 75.3 | 56.4 |
| | 4 | | | | 1.2 | 2 | 400 | 96 | 43.5 | 75.0 | 58.0 |
| Comparative Example 1 | 5 | 0 | 2 | 400 | | | | 0 | N/D | N/D | N/D |
| | 6 | | | | 1.2 | 2 | 400 | 24 | 42.0 | 73.5 | 57.2 |
| | 7 | | | | 1.2 | 2 | 400 | 48 | 34.8 | 63.7 | 54.6 |
| | 8 | | | | 1.2 | 2 | 400 | 72 | 31.5 | 65.3 | 48.2 |
| | 9 | | | | 1.2 | 2 | 400 | 96 | 30.1 | 66.0 | 45.6 |

N/D = Not Determined

Into a glass lined reactor fitted for stirring and temperature control is charged 94.56 g of $V_2O_5$ and sufficient isobutanol to form a slurry. $V_2O_5$ is then dissolved in the isobutanol by passing a stream of anhydrous hydrogen chloride gas while maintaining the temperature between 30° and 40° C. The resulting solution is red-brown colored and nearly saturated with hydrogen chloride gas. This solution is added to a solution containing 122.3 g of crystalline orthophosphoric acid dissolved in sufficient isobutanol to bring the total isobutanol content in the resulting mixture of solutions to 650 cc. The resulting solution is refluxed at about 110° C. for 1.5 hours. Thereafter, the reflux condenser is removed and isobutanol solvent is distilled from the reaction mixture. During the heating above at reflux and subsequently during distillation, hydrogen chloride gas evolves from the solution and is vented.

As the heating is continued and the volatiles, mainly isobutanol and hydrogen chloride, are evolved, the color of the solution continues to change; transitorally it assumes various shades of green or blue, the colorations associated with vanadium in the plus 4 valence (oxidation) state. Finally, after about two-thirds of the solvent has been evolved, the solution is colored a greenish-blue. Some light blue precipitate is usually present in the concentrate at this time. The remainder of the volatiles are conveniently removed by placing the concentrate in a loosely covered glass vessel in a ventillated oven maintained at 150° C. for about 7 hours. The resulting catalyst precursor is then sized to −10 +20 mesh (Tyler series) and 5 cc thereof placed in the reactor and activated in-situ under conditions of 400° C. while passing a gaseous mixture of 1.2 mole % n-butane in air (contact time 2 sec.). The yield results are summarized at Table 1, runs 1 to 4. Contact time during reaction is 2 sec. and feed gas is 1.2 mole % n-butane in air. Note that the hours on stream of Table 1 include activation for runs 1 to 4.

COMPARATIVE EXAMPLE 1

Example 1 is repeated with the exception that the dried catalyst precursor is activated by passing air alone (contact time 2 sec.) through the reactor 400° C. for 2 hrs. (see Table 1 run 5). After 2 hrs. the air stream is The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a vanadium phosphorus oxygen containing composition capable of catalyzing the oxidation of hydrocarbons which comprises:
   (a) reacting at least one vanadium containing compound with at least one phosphorus containing compound in a liquid organic media comprising at least one organic alcohol under substantially anhydrous conditions of less than about 5% by weight water based on the weight of the organic media in a manner and under conditions sufficient to form a vanadium phosphorus oxygen containing catalyst precursor composition having a phosphorus to vanadium atomic ratio of from about 0.5:1 about 2:1 and an average vanadium valence of from 3.9 to about 4.7, said vanadium and phosphorus containing compounds being dissolved in said liquid organic media during said reaction;
   (b) separating the catalyst precursor composition from the organic media; and
   (c) activating the catalyst precursor composition in the absence of air along by contact with an atmosphere comprising air and at least one hydrocarbon.

2. The process of claim 1 wherein the liquid organic media comprises at least one primary or secondary organic alcohol.

3. The process of claim 2 wherein the organic alcohol is isobutanol.

4. The process of claim 1 wherein the liquid organic media comprises at least one organic alcohol, the vanadium containing compound is vanadium pentoxide, and the phosphorus containing compound is phosphoric acid.

5. The process of claim 1 wherein said catalyst precursor is shaped into structures prior to activation.

6. The process of claim 1 wherein activation is conducted at temperatures of from about 200° to about 450° C.

7. The process of claim 1 wherein activation is conducted at temperatures of from about 250° to about 410° C.

8. The process of claim 1 wherein activation is conducted at temperatures of from about 300° to about 410° C.

9. The process of claim 1 wherein said activation atmosphere comprises a gaseous mixture of air and a hydrocarbon, wherein said hydrocarbon is the same hydrocarbon which will be oxidized by the catalyst.

10. The process of claim 1 wherein activation is conducted in a non-explosive gaseous mixture comprising air and a hydrocarbon selected from the group consisting of methane, ethane, propane, butane, butene, butadiene, pentane and mixtures thereof.

11. The process of claim 10 wherein activation is conducted in a gaseous mixture comprising air and from about 0.1 to about 1.8 mole % butane based on the total number of moles of the components in the gaseous mixture.

12. The process of claim 1 wherein said process is conducted in a manner and under conditions sufficient to impart to said activated catalyst a phosphorus to vanadium atomic ratio of from about 1:1 to about 1.4:1, an average vanadium valence of from 3.9 to about 4.2, and a surface area of greater than about 5 $m^2/g$.

13. The process of claim 1 wherein said vanadium containing compounds is $V_2O_5$ and is dissolved in said liquid organic media with a hydrogen halide acid for reaction with the phosphorus containing compound.

* * * * *